United States Patent [19]
Bruhn et al.

[11] 4,223,158

[45] Sep. 16, 1980

[54] 2,3,5-TRISUBSTITUTED CYCLOPENTANEALKENOIC ACIDS, DERIVATIVES THEREOF AND INTERMEDIATES THERETO

[75] Inventors: Mildred S. Bruhn, Niles; Raphael Pappo, Skokie, both of Ill.

[73] Assignee: G. D. Searle & Co., Skokie, Ill.

[21] Appl. No.: 35,966

[22] Filed: May 4, 1979

Related U.S. Application Data

[62] Division of Ser. No. 346,358, Mar. 30, 1973.

[51] Int. Cl.$^2$ .................... C07C 177/00; C07C 61/38; C07C 69/74
[52] U.S. Cl. ............................ 560/121; 260/410.9 R; 260/413; 562/503
[58] Field of Search .................. 260/410.9 R, 413; 560/121; 562/503

[56] References Cited

U.S. PATENT DOCUMENTS

| | | | |
|---|---|---|---|
| 3,832,380 | 8/1974 | Matsui et al. | 560/121 |
| 3,900,512 | 8/1975 | Sih | 560/121 |

*Primary Examiner*—Robert Gerstl
*Attorney, Agent, or Firm*—Mary Jo Kanady

[57] ABSTRACT

2,3,5-Trisubstituted cyclopentanealkenoic acids display anti-microbial activity, e.g. anti-bacterial and anti-fungal, and are, in addition, useful as intermediates in the manufacture of prostanoic acid derivatives.

6 Claims, No Drawings

2,3,5-TRISUBSTITUTED CYCLOPENTANEALKENOIC ACIDS, DERIVATIVES THEREOF AND INTERMEDIATES THERETO

This is a division of application Ser. No. 346,358, filed Mar. 30, 1973.

The present invention relates to a novel process and to novel intermediates utilized in that process. The products produced by the process of this invention are prostanoic acid derivatives as represented by the following structural formula

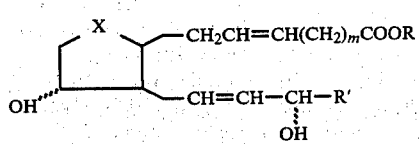

wherein X represents a carbonyl or hydroxymethylene radical, R represents hydrogen or a lower alkyl radical, R' is an alkyl radical containing 1 to 10 carbon atoms, m is a positive integer greater than 2 and less than 5, and the wavy lines indicate the alternative R and S stereochemical configurations.

The lower alkyl radicals represented by R in the foregoing structural formula are typified by methyl, ethyl, propyl, butyl, pentyl, hexyl, heptyl and the branched-chain groups isomeric therewith.

In the instant process there are produced novel intermediates represented by the following structural formula

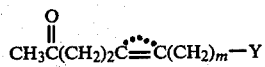

wherein Y represents a cyano or carboxy radical, m represents a positive integer greater than 2 and less than 5 and the dotted line is indicative of a doubly or triply bonded unsaturated linkage. Those intermediates are useful also in consequence of their anti-microbial, anti-fungal, anti-bacterial and anti-algal properties. Those properties are apparent from the activity of the compounds in the assays described in detail in U.S. Pat. Nos. 3,652,606; 3,668,251; 3,679,697 and 3,692,799.

The manufacture of the latter novel intermediates is exemplified by the consecutive synthetic steps involving first, reaction of 5-chloropent-1-yne with butyl lithium to form the corresponding lithium acetylide, reaction of that organometallic compound with boron trifluoride or boron trichloride to afford the tri-(5-chloropent-1-ynyl) boron derivative, which is reacted with methyl vinyl ketone to afford 9-chloro-5-nonyn-2-one, reaction of the latter substance with sodium cyanide in aqueous ethanol to yield 9-cyano-5-nonyn-2-one, saponification of that nitrile with aqueous sodium hydroxide in ethanol to produce 9-oxo-5-decynoic acid, followed by reduction of the olefinic double bond, thus affording the 9-oxo-5-decenoic acids. The cis-acid is conveniently produced by catalytic hydrogenation, e.g. with a palladium-on-barium sulfate catalyst in the presence of a catalyst poison such as quinoline, while the trans-acid is obtained by chemical reduction, e.g. with sodium and liquid ammonia.

There are also produced by the present process novel intermediates of the following structural formula

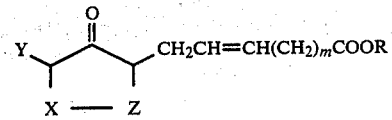

and the enol ethers corresponding. In that formula X represents a carbonyl or hydroxymethylene radical, Y is hydrogen or a methoxalyl radical, R is hydrogen or a lower alkyl radical, m is a positive integer greater than 2 and less than 5 and Z is a carbonyl or methine radical. These compounds are useful also in consequence of their anti-microbial, e.g. anti-bacterial and anti-fungal properties, as evidenced by their activity in the assays described in detail in U.S. Pat. Nos. 3,668,241; 3,679,687 and 3,692,799.

The latter novel intermediates are conveniently manufactured by processes as typified by reaction of the aforementioned 9-oxo-5-decenoic acids with dimethyl oxalate to produce the 7-(2,3,5-trioxo-4-methoxalylcyclopentane)hept-5-enoic acids, cleavage of the methoxalyl function by heating at elevated temperature with dilute hydrochloric acid to produce the 7-(2,3,5-trioxocyclopentane)hept-5-enoic acids, selective reduction of the 3-oxo function, utilizing sodium borohydride, to produce the 7-(2,5-dioxo-3-hydroxycyclopentane)hept-5-enoic acids, esterification with concomitant formation of the enol ether function by reaction with acetone dimethyl ketal to afford the methyl 7-(4-hydroxy-2-methoxy-5-oxocyclopent-1-ene)hept-5-enoates followed by reduction with sodium dihydro bis-(2-methoxyethoxy)aluminate in benzene to produce the methyl 7-(3-hydroxy-5-oxocyclopent-1-ene)hept-5-enoates.

The latter intermediates are conveniently converted to the corresponding prostanoic acid derivatives by reaction with an alkenyl copper reagent represented by the following structural formula

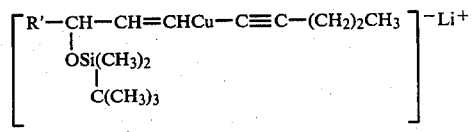

The manufacture of the latter reagents is described by Corey and Beames, *J. Am. Chem. Soc.*, 94, 7210 (1972). An example of the manufacture of a typical prostanoic acid derivative is the reaction of an aforementioned methyl 7-(2-hydroxy-5-oxocyclopent-1-ene)hept-5-enoate with dihydropyran to afford the corresponding 3-tetrahydropyran-2'-yl ether and reaction of that ether with lithium (1-pentynyl)-(3-dimethyltertiarybutylsilyloxy-1-octenyl) cuprate to afford methyl 7-[(3-tetrahydropyran-2'-yloxy]-2-(3-dimethyltertiarybutylsilyloxy-1-octenyl)-5-oxocyclo=pent-1-ene)hept-5-enoate. Removal of the protecting groups by reaction with acetic acid affords the desired methyl 7-{3(RS)-hydroxy-2-[3(SR)-hydroxy-1-octenyl]-5-oxocyclopentane}hept-5-enoate and methyl 7-{3(RS)-hydroxy-2-[3(RS)-hydroxy-1-octenyl]-5-oxocyclopentane}hept-5-enoate.

The invention will appear more fully from the examples which follow. These examples are set forth by way of illustration only and are not to be construed as limiting the invention either in spirit or in scope as many modifications both in materials and methods will be apparent to those skilled in the art. In these examples temperatures are given in degrees Centigrade (°C.) and materials in parts by weight, unless otherwise noted.

EXAMPLE 1

14.85 Parts of 5-chloropent-1-yne is dissolved in 250 parts by volume of toluene and the resulting solution is cooled to approximately −40°. To that solution is then added 62.8 parts by volume of 2.31 M ethereal butyl lithium and stirring is continued for approximately 15 minutes. 6.87 Parts of boron trifluoride etherate is added and the reaction mixture is stirred for about 2 hours, then allowed to stand for about 16 hours at −5° to −10°. At the end of that time 10.14 parts of methyl vinyl ketone is added at −40° and the reaction mixture is stirred for about 4 hours, then is quenched with water. 50 Parts by volume of 3 N hydrochloric acid is added and the mixture is kept at room temperature for about 16 hours, at the end of which time the aqueous and organic layers are separated. The aqueous layer is extracted with toluene and the organic layer with water. The organic solutions are combined, washed successively with aqueous sodium hydroxide and water, then dried over anhydrous sodium sulfate and stripped to dryness under reduced pressure, thus affording the crude product. This material is purified by distillation under reduced pressure to afford 9-chloro-5-nonyn-2-one, boiling at about 80°–92° at a pressure of 0.11–0.06 mm.

EXAMPLE 2

To a solution consisting of 2.77 parts of 9-chloro-5-nonyn-2-one in 8 parts by volume of ethanol is added a solution containing 2.77 parts of sodium cyanide dissolved in 4 parts of water. The resulting reaction mixture is heated at 80°–100° for about 24 hours, then is cooled and diluted with ether, whereupon 20 parts by volume of dilute aqueous sodium hydroxide is added with stirring. The layers are separated and the alkaline layer extracted with ether. The ether extracts are combined, then washed with water, dried over anhydrous sodium sulfate and concentrated under reduced pressure to afford 9-cyano-5-nonyn-2-one. This compound exhibits an infrared absorption maximum at 2250 reciprocal centimeters and nuclear magnetic resonance peaks at δ2.18 and δ2.50.

EXAMPLE 3

A mixture consisting of 1.79 parts of 9-cyano-5-nonyn-2-one, 5 parts by volume of ethanol and 5 parts by volume of 5% aqueous sodium hydroxide is heated just below the reflux temperature for about 6 hours, then is cooled and extracted with chloroform. The alkaline layer is acidified by means of hydrochloric acid to pH 4, resulting in separation of a brown liquid. This material is extracted with chloroform and the chloroform solution is washed with water, dried over anhydrous sodium sulfate, then concentrated to dryness under reduced pressure to afford 9-oxo-5-decynoic acid. It exhibits nuclear magnetic resonance peaks at δ2.18 and δ2.50.

EXAMPLE 4

To a solution of 23.6 parts of 9-oxo-5-cis-decynoic acid in a mixture of 999 parts by volume of benzene and 221.4 parts by volume of 1% quinoline in benzene is added 1.18 parts of 5% palladium-on-barium sulfate catalyst and the resulting mixture is shaken with hydrogen at atmospheric pressure and room temperature until one molecular equivalent of hydrogen is absorbed. The catalyst is then removed by filtration and the filtrate is washed successively with dilute hydrochloric acid and water, then dried over anhydrous sodium sulfate and stripped of solvent under reduced pressure, thus producing 9-oxo-5-cis-decenoic acid, which exhibits nuclear magnetic resonance maxima at δ2.13 and δ5.39.

EXAMPLE 5

A solution of potassium tertiary-butoxide is prepared by dissolving 4.8 parts of potassium metal in 30 parts by volume of tertiary-butyl alcohol at reflux temperature under nitrogen. To that solution is then added a solution consisting of 3.7 parts of 9-oxo-5-cis-decenoic acid and 7.23 parts of dimethyl oxalate dissolved in 25 parts by volume of tertiary-butyl alcohol. The addition is conducted with stirring at the reflux temperature. After the reaction mixture is refluxed under nitrogen for about 2½ hours, the colored supernatant is decanted and the precipitate is dissolved in water, then acidified with dilute hydrochloric acid. Extraction of that acidic mixture with chloroform affords an organic solution, which is washed with saturated aqueous sodium chloride, then dried over anhydrous sodium sulfate and stripped of solvent under reduced pressure to afford 7-(2,3,5-trioxo-4-methoxalylcyclopentane)hept-5-cis-enoic acid, melting at about 99°–104° and represented by the following structural formula

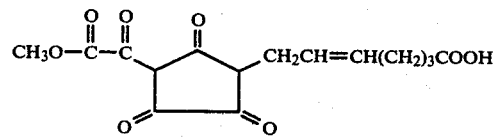

EXAMPLE 6

A mixture consisting of 10.6 parts of 7-(2,3,5-trioxo-4-methoxalylcyclopentane)hept-5-cis-enoic acid and 490 parts by volume of dilute hydrochloric acid is heated at the reflux temperature for about 3 hours, then is cooled and extracted with ethyl acetate. The organic extract is washed with saturated aqueous sodium chloride, then dried over anhydrous sodium sulfate and stripped of solvent under reduced pressure to afford the crude product. Purification of that material is effected by adsorption on a silicic acid chromatographic column followed by elution with ethyl acetate-benzene. From the eluate there are obtained pale yellow crystals of 7-(2,3,5-trioxocyclopentane)hept-5-cis-enoic acid, melting at about 84°–85°. This compound is represented by the following structural formula

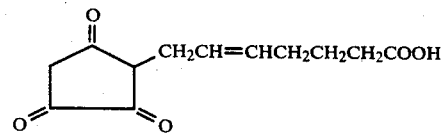

EXAMPLE 7

A solution of 0.54 part of 7-(2,3,5-trioxocyclopentane)hept-5-cis-enoic acid in 11 parts of water is neutralized by the addition of dilute aqueous sodium hydroxide and that neutralized solution is cooled to 0°–5°, at which point 0.037 part of sodium borohydride is added. The reaction mixture is stirred at 0°–5° for about 50 minutes, then is quenched by the addition of dilute hydrochloric acid to pH 1. The resulting solution is extracted several times with ethyl acetate. The ethyl acetate extracts are combined, washed with saturated aqueous sodium chloride, dried over anhydrous sodium sulfate and concentrated to dryness under reduced pressure to afford white crystals of 7-(2,5-dioxo-3-hydroxycyclopentane)-hept-5-cis-enoic acid, melting at about 83°–85° and represented by the following structural formula

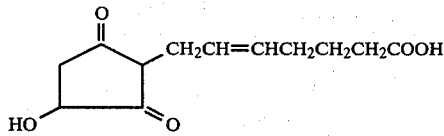

EXAMPLE 8

To a solution of 2.99 parts of 7-(2,5-dioxo-3-hydroxycyclopentane)hept-5-cis-enoic acid in 33.8 parts by volume of methanol, under nitrogen, is added, with stirring, 10.18 parts by volume of acetone dimethyl ketal followed by 3.97 parts by volume of 1.14% methanolic hydrogen chloride. The resulting reaction mixture is allowed to stand at room temperature for about 48 hours, then is stripped of solvent by distillation under reduced pressure. A small amount of ether is added and the mixture is allowed to stand for about 48 hours, then is dissolved in benzene containing 1% triethylamine and that solution is washed successively with dilute aqueous potassium carbonate and water, then dried over anhydrous sodium sulfate and stripped of solvent under reduced pressure to afford white crystals of methyl 7-(4-hydroxy-2-methoxy-5-oxocyclopent-1-ene)hept-5-cis-enoate, melting at about 77°–78° and represented by the following structural formula

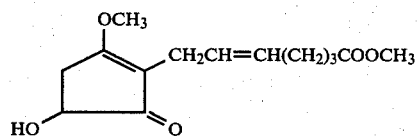

It exhibits nuclear magnetic resonance maxima at δ3.69, δ3.98, δ4.29 and δ5.39.

EXAMPLE 9

To a solution of 0.256 part of methyl 7-(4-hydroxy-2-methoxy-5-oxocyclopent-1-ene)hept-5-cis-enoate in a mixture consisting of 3.7 parts by volume of tetrahydrofuran and 4.4 parts by volume of toluene, under nitrogen, is added, dropwise at −70°, 0.33 parts by volume of a 3.3 M sodium dihydro bis-(2-methoxyethoxyaluminate in benzene solution. Stirring is continued at that temperature for about 5½ hours, at the end of which time the reaction mixture is quenched by the addition of methanol. After an additional 10 minute stirring period, the mixture is allowed to warm to room temperature, then is acidified to pH 2 by the addition of dilute hydrochloric acid. The resulting two phase mixture is extracted with ethyl acetate and the organic extract is washed with saturated aqueous sodium chloride, then dried over anhydrous sodium sulfate and stripped of solvent under reduced pressure to afford the crude product. That material is purified by adsorption on a silicic acid chromatographic column followed by elution with ethyl acetate in benzene to afford, as an oil, methyl 7-(3-hydroxy-5-oxocyclopent-1-ene)hept-5-cis-enoate. It is represented by the following structural formula

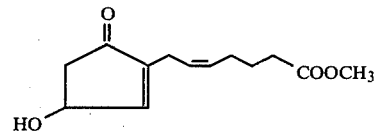

It exhibits nuclear magnetic resonance maxima at δ3.68, δ5.57 and δ7.19.

EXAMPLE 10

To a solution of 0.288 part of 7-(3-hydroxy-5-oxocyclopent-1-ene)hept-5-cis-enoate in 3.6 parts by volume of ether is added 0.01 part of p-toluenesulfonic acid and 0.109 part of dihydropyran. The reaction mixture is allowed to stand at room temperature for about 24 hours, then is diluted with water, washed successively with 5% aqueous potassium carbonate and water, dried over anhydrous sodium sulfate and stripped of solvent under reduced pressure. The resulting product is methyl 7-(3-tetrahydropyran-2'-yloxy-5-oxocyclopent-1-ene)hept-5-cis-enoate.

EXAMPLE 11

To a solution of 0.463 part of 3-methyltertiarybutylsilyloxy-1-octenyl iodide in 3.2 parts by volume of ether is added, at −65° in an atmosphere of nitrogen, 2.44 parts by volume of 1.03 N-ethereal tertiary-butyl lithium. To that mixture is then added, over a period of about 30 seconds, the complex formed by the reaction of 0.164 part of 1-pentynyl copper and 0.409 part of hexamethyl posphorous triamide dissolved in 3.2 parts by volume of ether. The resulting reaction mixture is stirred at −65° for about 10 minutes, at the end of which time 0.202 part of 7-(3-tetrahydropyran-2'-yloxy-5-oxocyclopent-1-ene)hept-5-cis-enoate is added. Stirring is continued at −65° for about 1 hour, at the end of which time the reaction mixture is warmed slightly, then poured into a mixture of ethyl acetate and dilute hydrochloric acid. The ethyl acetate layer is separated, then washed with water, dried over anhydrous sodium sulfate and stripped to afford methyl 7-[(3-tetrahydropyran-2'-yloxy)-2-(3-dimethyltertiarybutylsilyloxy-1-octenyl)-5-oxocyclopent-1-ene]hept-5-cis-enoate.

EXAMPLE 12

A solution of 0.242 part of methyl 7-[(3-tetrahydropyran-2'-yloxy)-2-(3-dimethyltertiarybutylsilyloxy-1-octenyl)-5-oxocyclopent-1-ene]hept-5-cis-enoate in 1.5 parts by volume of 3:1:1 acetic acid-tetrahydrofuran-water is allowed to stand at room temperature for about 16 hours. At the end of that time the reaction mixture is diluted with benzene-ether and that solution is washed successively with water, aqueous potassium carbonate and water, then dried over anhydrous sodium sulfate and stripped of solvent under reduced pressure, thus affording methyl 7-{[3(RS)-hydroxy-2-[3(RS)-hydroxy-1-octenyl]-5-oxocyclopentane]}hept-5-cis-enoate and 7-{[3(RS)-hydroxy-2-[3(SR)-hydroxy-1-octenyl]-5-oxocyclopentane]}hept-5-cis-enoate. Nuclear magnetic resonance maxima are observed at about δ2.64, δ2.71, δ2.82, δ2.89, δ3.69, δ4.06, δ5.37 and δ5.60.

EXAMPLE 13

To a solution of 1.82 parts of 9-oxo-5-decynoic acid in 40 parts by volume of 50% aqueous ethanol is added 0.53 part of anhydrous sodium carbonate and the resulting solution is concentrated to dryness under reduced pressure. The residue is thoroughly dried, then is mixed with 200 parts by volume of anhydrous ammonia and that mixture is stirred vigorously at approximately −70° while 0.46 part of sodium metal is added in small portions. When the absence of unreacted sodium is indicated by disappearance of the characteristic blue color, the ammonia is removed under an atmosphere of nitrogen and dilute hydrochloric acid is added to the residue. That acidic mixture is extracted with benzene and the benzene extracts are combined, washed with water, dried over anhydrous sodium sulfate and stripped of solvent under reduced pressure to afford 9-oxo-5-trans-decenoic acid.

EXAMPLE 14

The substitution of 9-oxo-5-trans-decenoic acid in the procedure of Example 5 and reaction of the successive intermediates produced in Examples 5–12 according to the procedures of those Examples affords methyl 7-{[3(RS)-hydroxy-2-[3(SR)-hydroxy-1-octenyl]-5-oxocyclopentane]}hept-5-trans-enoate and methyl-{[3(RS)-hydroxy-2-[3(RS)hydroxy-1-octenyl]-5-oxocyclopentane]}hept-5-trans-enoate.

EXAMPLE 15

When 0.14 part of lithium metal is substituted for sodium metal in the procedure of Example 13, 9-oxo-5-trans-decenoic acid is, similarly, obtained.

EXAMPLE 16

To a solution of 0.238 part of methyl 7-(3-hydroxy-5-oxocyclopent-1-ene)hept-5-cis-enoate in 4 parts by volume of isopropyl alcohol is added a solution consisting of 0.04 part of sodium hydroxide in 1 part of water and the resulting reaction mixture is allowed to stand, in an atmosphere of nitrogen, at 0°–5° for about 16 hours. At the end of that time the reaction mixture is acidified by the addition of 1.1 parts by volume of 1 N hydrochloric acid, then is concentrated to a small volume at room temperature under reduced pressure. Extraction of that acidic mixture with ethyl acetate affords an organic solution, which is washed with aqueous sodium chloride, dried over anhydrous sodium sulfate and evaporated to dryness under reduced pressure, thus affording the crude product. Purification of that substance is effected by adsorption on a silicic acid chromatographic column followed by elution with ethyl acetate in benzene, thus affording 7-(3-hydroxy-5-oxo-cyclopent-1-ene)hept-5-cis-enoic acid.

What is claimed is:

1. A compound of the formula

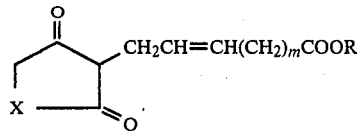

wherein X represents a carbonyl or hydroxymethylene radical, R is hydrogen or a lower alkyl radical and m is a positive integer greater than 2 and less than 5.

2. As in claim 1 a compound of the formula

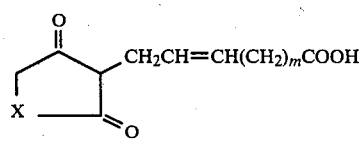

wherein X represents a carbonyl or hydroxymethylene radical and m is a positive integer greater than 2 and less than 5.

3. As in claim 1, a compound of the formula

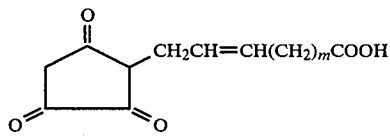

wherein m is a positive integer greater than 2 and less than 5.

4. As in claim 1, the compound which is 7-(3-hydroxy-2,5-dioxocyclopentane)hept-5-cis-enoic acid.

5. As in claim 1, the compound which is 7-(2,3,5-trioxocyclopentane)hept-5-cis-enoic acid.

6. The compound which is methyl 7-(4-hydroxy-2-methoxy-5-oxocyclopent-1-ene)hept-5-cis-enoate.

* * * * *